(12) United States Patent
Bongs et al.

(10) Patent No.: US 6,852,513 B1
(45) Date of Patent: Feb. 8, 2005

(54) METHOD FOR EXTRACTING AN INSULIN USING ENZYMES WHICH ARE BONDED TO A NON-POROUS POLYMER SUPPORT

(75) Inventors: Jürgen Bongs, Wiesbaden (DE); Johannes Meiwes, Idstein (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/700,391

(22) PCT Filed: May 3, 1999

(86) PCT No.: PCT/EP99/02973

§ 371 (c)(1),
(2), (4) Date: Nov. 14, 2000

(87) PCT Pub. No.: WO99/60150

PCT Pub. Date: Nov. 25, 1999

(30) Foreign Application Priority Data

May 15, 1998 (DE) ......................... 198 21 866

(51) Int. Cl.⁷ .............................. C12N 15/09
(52) U.S. Cl. ...................... 435/69.4; 435/181; 435/174; 435/68.1; 435/180
(58) Field of Search ............................. 435/174, 180, 435/181, 69.4, 68.1

(56) References Cited

U.S. PATENT DOCUMENTS

| | | | |
|---|---|---|---|
| 4,994,388 A | 2/1991 | Hillegas et al. | |
| 5,547,929 A | 8/1996 | Anderson, Jr. et al. | |
| 5,641,639 A | * 6/1997 | Perry | 435/7.92 |

FOREIGN PATENT DOCUMENTS

EP          0294 851 A2     12/1988

OTHER PUBLICATIONS

Graessel et al., Analytical Biochemistry (1989), 180(1), 72–8.*
Mandosa, R., "Insulin Analogs: Genetic Engineering for Diabetes Control," Diabetes Wellness Letter, Nov. 1998, pp. 1–6.
www.accessdata.fda.gov/scripts/cder/ob/docs/temptn.cfm.
Alexander Huwig et al., "Laboratory procedures for producing 2–keto–D–glucose, 2–keto–D–xylose and 5–keto–D–fructose from D–glucose, D–xylose and L–sorbose with immobilized pyranose oxidase of Peniophora gigantea," Journal of Biotechnology 32(3):309–315 (1994).
P. Chr. Lorenzen et al., "Characterization of trypsin immobilized on ixirane–acrylic beads for obtaining phosphopeptides from casein," Z. Ernährungswiss 34(2):118–130 (1995).
H. Eckstein et al., "Immobilization of Papain and Trypsin on Epoxy–Polymers for Enzyme–Catalyzed Peptide Synthesis," Chemistry of Peptides and Proteins vols. 5/6(A):211–216 (1993).
Derwent Abstract of EP 0294 851 A2.

* cited by examiner

Primary Examiner—Irene Marx
(74) Attorney, Agent, or Firm—Finnegan, Henderson, Farabow, Garrett, & Dunner L.L.P.

(57) ABSTRACT

The invention relates to a method for catalysing complex reactions or large molecules, more specifically, to enzyme-catalysed reactions during which undesirable consecutive or subsidiary reactions usually occur; using enzymes which are bonded to a polymer support. According to the invention, undesirable consecutive or subsidiary reactions are to a large extent avoided by selecting a non-porous or almost non-porous support material. In particular, the invention relates to a method for the enzymatic extraction of biomolecules, preferably peptides, proteins, oligosaccharides or polysaccharides from their biologically inactive precursors using enzymes which are bonded to a polymer support, especially a method for extracting insulins or their analogs from the corresponding precursors using enzymes which are bonded to a polymer support. As a result of selecting a non-porous almost non-porous support material, this method leads to a selective formation of biomolecules, especially of insulins or insulin analogs and corresponding valuable substances which can be split into said insulins or their analogs, undesirable consecutive or subsidiary reactions being to a large extent avoided.

9 Claims, 7 Drawing Sheets

Figure 1A:
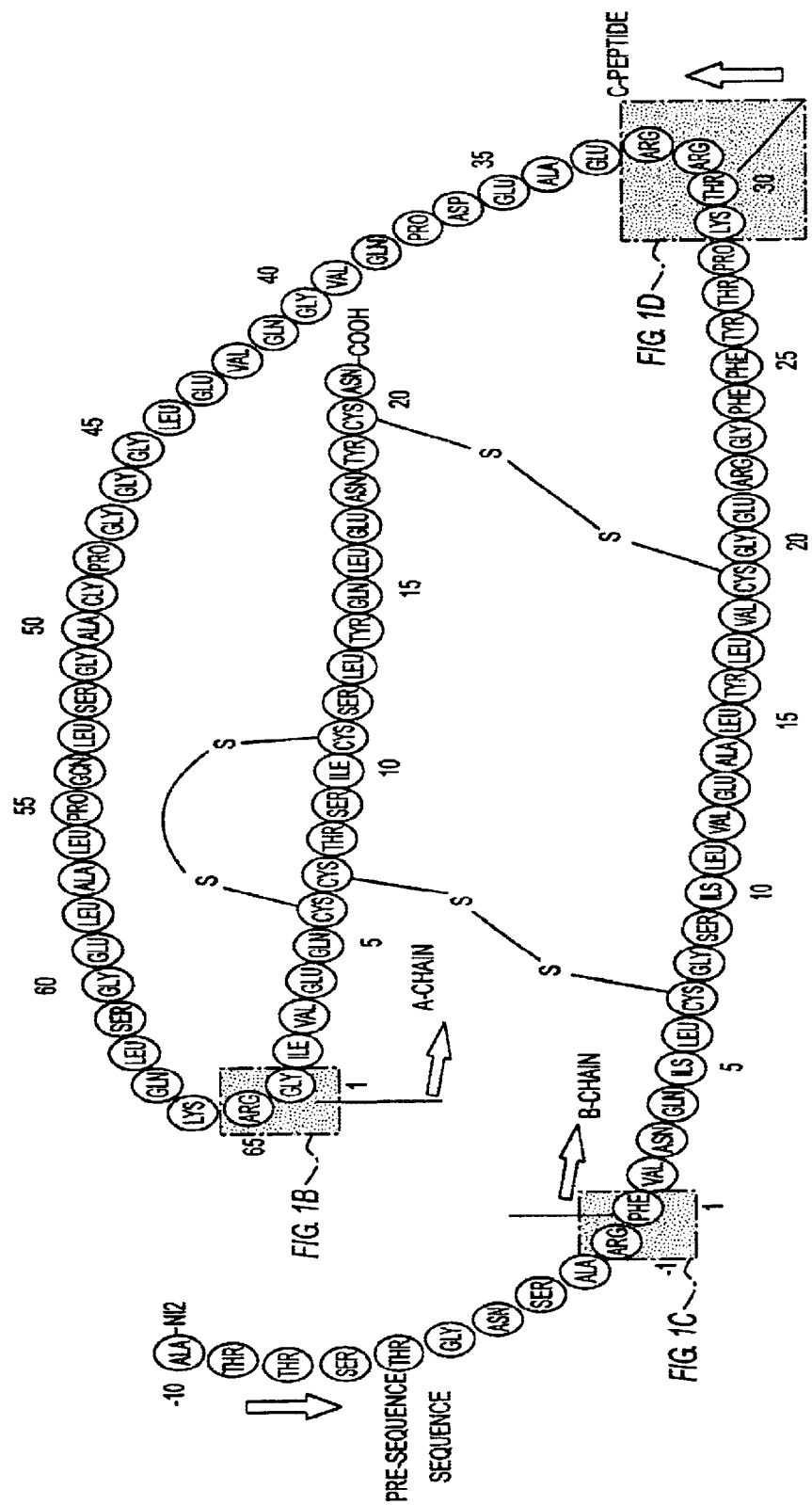

METHOD FOR EXTRACTING AN INSULIN USING ENZYMES WHICH ARE BONDED TO A NON-POROUS POLYMER SUPPORT

This application is a 371 of PCT/EP99/02973, filed May 3, 1999.

The present invention relates to a process for the catalysis of complex reactions of large molecules, namely reactions having undesirable secondary or side reactions, by means of enzymes bonded to a polymeric support and in particular to a process for the enzymatic obtainment of biomolecules, in particular of biologically active peptides, for example of insulins or their analogs, of proteins, oligosaccharides or of polysaccharides, from their biologically inactive precursors, for example preproinsulins, by means of enzymes bonded to a polymeric support.

The preparation of human insulin and its derivatives by means of different approaches is described in the literature. In addition to chemical synthesis, which is uneconomical on account of the complexity of the target molecule, a semisynthetic and a genetic engineering process furthermore exist.

In the semisynthetic approach, a replacement of the C-terminal amino acid of the B chain of porcine insulin catalyzed by trypsin occurs, which leads to the formation of human insulin (H.-D. Jakubke et al., Angew. Chem., 97 (1985) 79).

The genetic engineering approach to the preparation of human insulin proceeds via the stage of preproinsulin and its derivatives, which are likewise subjected to a tryptic cleavage in the work-up (B. H. Frank et al., Peptides: synthesis, structure, function, (1981) 729–738; Jonasson et al., Eur. J. Biochem., 236 2 (1996) 656–661; Kemmler et al., J. Biol. Chem., 246 (1971) 6786–6791).

For efficient utilization of the enzyme, for the semisynthetic approach a process was developed which allows the use of immobilized trypsin (EP O 294 851).

For the obtainment of insulins or their analogs from the corresponding preproinsulins prepared by genetic engineering, as yet no enzymatic process is known in which the enzyme trypsin is present in immobilized form, so that in known processes, on the one hand, new trypsin must be added for each new reaction batch and, on the other hand, a laborious depletion of the enzyme is necessary in the course of product purification.

The tryptic cleavage of preproinsulin (PPI) is a complex, enzyme-catalyzed reaction with numerous undesirable secondary and side reactions. As shown in FIGS. 1A–1D, on account of the numerous reactive sites, a large number of reaction products are formed in the tryptic cleavage of PPI, of which the compounds Arg(B31), Arg(B32)-insulin ("di-Arg") and Arg(B31)-insulin ("mono-Arg") are to be regarded as the actual valuable substances for further work-up. Thus, removal both of the presequence and of the "middle" C chain (the C chain arranged in the preproinsulin between the sequence of the A chain and the sequence of the B chain of the insulin) is necessary. If cleavage reactions occur in other sites of the PPI, undesirable by-products are formed, such as, for example, des(B30)-insulin ("des-Thr").

While the cleavage with native trypsin leads to the predominant formation of the two valuable substances, Arg(B31), Arg(B32)-insulin ("di-Arg") and Arg(B31)-insulin ("mono-Arg"), the use of trypsin-immobilizates based on conventional supports such as, for example, Eupergit® C250L, Eupergit® C, Deloxan® leads to an unsatisfactory reaction pattern. The two valuable substances di- and mono-Arg are only formed in small amounts here, while the undesirable secondary or by-products (principally des-Thr) are primarily formed.

It is the object of the present invention to make available a process for the catalysis of complex reactions of large molecules, namely enzyme-catalyzed reactions, in which, as a rule, undesired secondary or side reactions occur, by means of enzymes bonded to a polymeric support, in which the undesired secondary or side reactions are avoided to the greatest extent. In particular, it is an object of the present invention to make available a process for the enzymatic obtainment of biomolecules, preferably of peptides, proteins, oligosaccharides or polysaccharides, from their biologically inactive precursors by means of enzymes bonded to a polymeric support, in particular a process for the obtainment of insulins or their analogs from the corresponding precursors by means of enzymes bonded to a polymeric support, which leads, with avoidance to the greatest extent of secondary or side reactions, to a selective formation of the biomolecules, in particular of the insulins or of the insulin analogs, and to the associated valuable substances which can be cleaved to give insulins for their analogs.

The object is achieved by a process for the catalysis of complex reactions of large molecules, in which, as a rule, undesired secondary or side reactions occur, by means of enzymes bonded to a polymeric support, wherein the polymeric support material has no or almost no pores which are large enough that the enzymes can bind to the support within these pores.

The object is further achieved by a process for the enzymatic obtainment of biomolecules selected from the group consisting of peptides, proteins, oligosaccharides or polysaccharides, from their precursors by means of one or more enzymes bonded to a polymeric support, wherein the polymeric support material has no or almost no pores which are large enough that the enzymes can bind to the support within these pores.

The process according to the invention is preferably suitable for the obtainment of insulins or their analogs from the corresponding precursors, in particular the preproinsulins, by means of one or more enzymes bonded to a polymeric support.

Insulin analogs are derived from naturally occurring insulins, namely human insulin or animal insulins, for example porcine or bovine insulin, by substitution or absence of at least one naturally occurring amino acid residue and/or addition of at least one amino acid residue to the A and/or B chain of the naturally occurring insulin.

Preferably, the polymeric support material is a copolymer of the monomers methacrylamide and N,N'-bis (methacrylamide), the polymeric support material particularly preferably having oxirane group-containing monomers.

In the process according to the invention, the enzyme is preferably bonded to the support material covalently with the aid of oxirane groups.

In the preferred process for the obtainment of insulins or their analogs from the corresponding precursors, in particular the preproinsulins, the enzyme used is preferably trypsin.

In this case, the enzyme immobilized on the support preferably has an activity of 0.05 to 0.5 U/ml and the pH of the reaction solution is preferably 6 to 10, particularly preferably 7 to 9.

The present invention is illustrated in greater detail below, in particular by means of the examples.

In a number of immobilizations, trypsin was covalently bonded to different support materials (Eupergit® C, Eupergit® 250L, Deloxan®).

The use of these immobilizates in the cleavage of pre-proinsulin (PPI), however, yielded the desired valuable substances di- or mono-Arg in only a small amount, despite variation of various reaction parameters such as, for example, pH, temperature or enzyme concentration. Instead of this, undesired by-products such as, for example, des-Thr were predominantly formed.

When using trypsin which was immobilized on the support Eupergit® C1Z, a pore-free support, the PPI cleavage surprisingly took place according to the pattern as desired in native use.

The choice of a pore-free support, for example Eupergit® C1Z, in the immobilization of trypsin thus for the first time allows the repeated use of the enzyme with simultaneously very good selectivity in the PPI cleavage in favor of the two valuable substances di- and mono-Arg. A use of the immobilized trypsin analogous to the semisynthetic process with the consequence of easy separability of the catalyst from the reaction solution and of repeated use is thus possible for the genetic engineering process for the preparation of human insulin.

EXAMPLES

Example 1 Immobilization of Proteins on Polymeric Supports

Example 1.1 Deloxan®

The immobilization of proteins on Deloxan® requires a prior activation of the support with glutaraldehyde. During the actual attachment of the enzyme, the given native activity of the trypsin was varied in a series of measurements.

$$\text{Activation: } pH = 9 \ [KPP: 100 \text{ mM}]$$
$$T = 25° \text{ C.}$$
$$t = 1 \text{ h}$$
$$\text{Deloxan®} = 10 \text{ g } [VR = 150 \text{ ml}]$$
$$GD = 0.2 \text{ g/g of TM}$$

$$\text{Attachment conditions: } pH = 9 \ [KPP: 100 \text{ mM}]$$
$$T = 25° \text{ C.}$$
$$t = 3 \text{ h}$$

Example 1.2 Eupergit® C250L and Eupergit® C

In the immobilization of trypsin on Eupergit® supports, the support suspension is mixed with the enzyme solution in a single-stage reaction. Attachment conditions for Eupergit® C250L:

$$pH = 8 \ [KPP: 1 \text{ M}]$$
$$T = 25° \text{ C.}$$
$$t = 3 \text{ d}$$

Attachment Conditions for Eupergit® C:

$$pH = 8.5 \ [\text{Borate buffer } 100 \text{ mM}]$$
$$T = 25° \text{ C.}$$
$$t = 3 \text{ d}$$
$$\text{Benzamidine} = 24 \text{ mM}$$

Example 1.3 Eupergit®) C1Z

The support Eupergit® C1Z is distinguished in contrast to the other supports by freedom from pores.

Attachment Conditions:

$$pH = 8 \ [KPP: 1 \text{ M}]$$
$$T = 25° \text{ C.}$$
$$t = 3 \text{ d}$$
$$\text{nat. trypsin} = 7400 \text{ U/g of TM } \left[\sum = 37{,}000 \text{ U to 5 g}\right]$$

Under the given conditions, a spec. activity of 405 U/g of TM is achieved. While the attachment yield is comparable to the results of the two other Eupergit®) supports, the recovery rate at 46% is clearly higher.

Example 2

A volume of 1 l of the preproinsulin solution having a concentration of 0.83 mg/ml is introduced into a glass beaker. After a pH of 8.3 has been set, the cleavage reaction is started by addition of the trypsin attached to Deloxan® in a concentration of 0.81 U/ml. The temperature of the solution is 6° C. over the entire reaction period. The pH is kept constant during the reaction by addition of 1 M NaOH solution. Samples of the reaction solution are withdrawn at regular intervals over a period of 23 h and the content of the individual reaction components is determined by means of HPLC.

Figure 2:
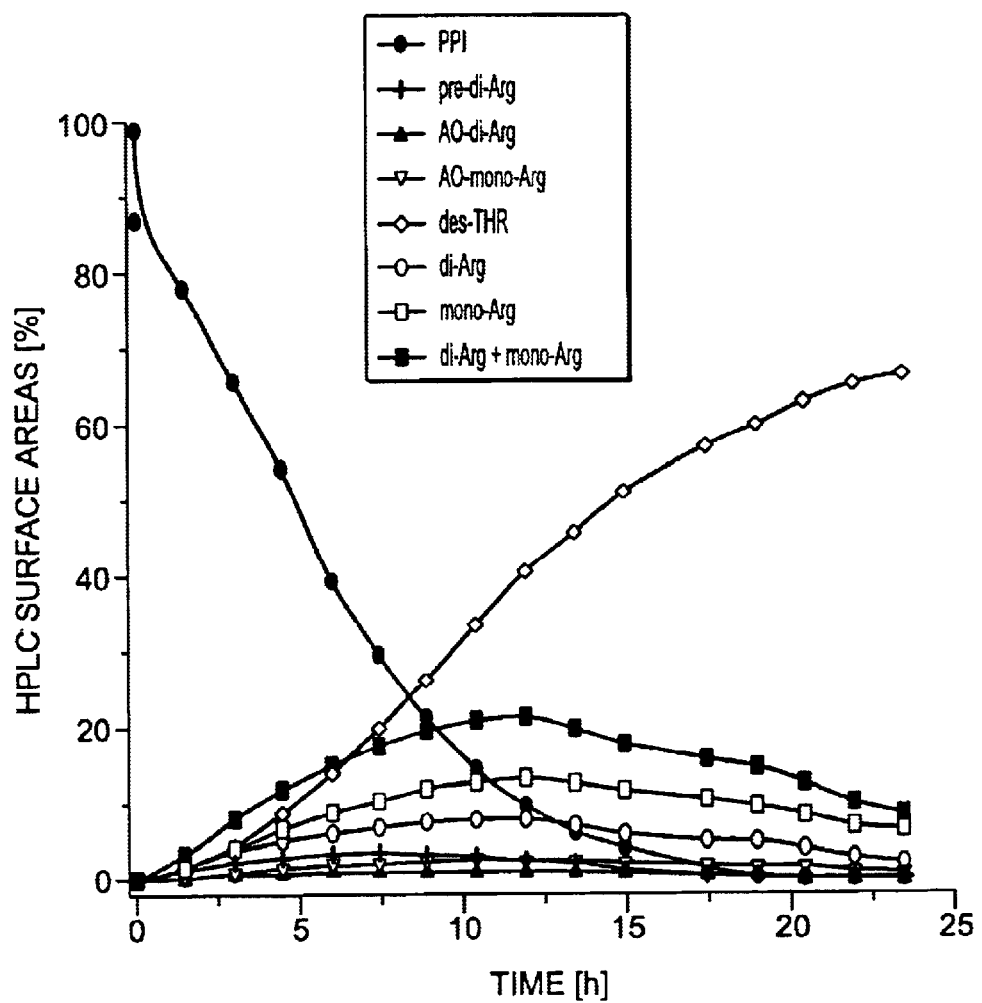

As can be seen in FIG. 2, des-Thr is formed as the main product over the period considered, while the amount of the two valuable substances di- and mono-Arg is clearly lower.

Example 3

A volume of 1 l of the preproinsulin solution having a concentration of 0.83 mg/ml is introduced into a glass beaker. After a pH of 8.3 has been set, the cleavage reaction is started by addition of the trypsin attached to Eupergit® C250L in a concentration of 1.62 U/ml. The temperature of the solution is 6° C. over the entire reaction period. The pH is kept constant during the reaction by addition of 1 M NaOH solution. Samples of the reaction solution are withdrawn at regular intervals over a period of 23 h and the content of the individual reaction components is determined by means of HPLC.

Figure 3:
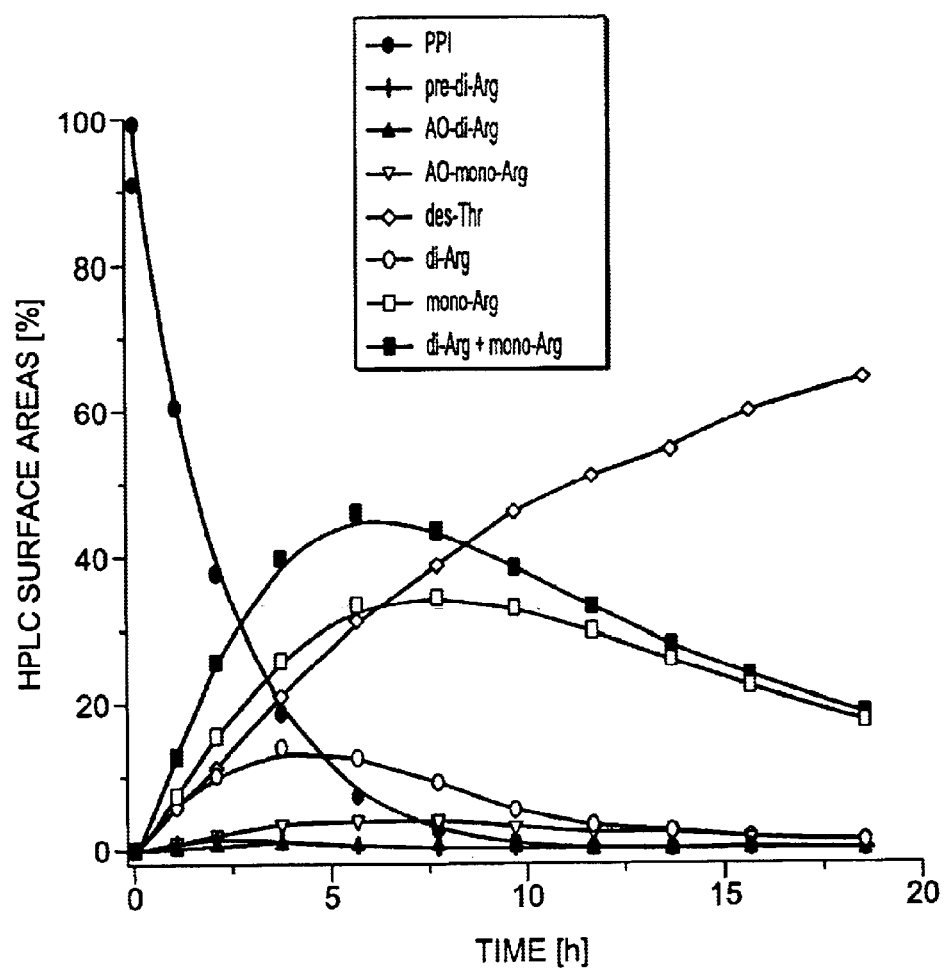

As can be seen in FIG. 3, des-Thr is also formed as a main product in this case over the period considered, while the amount of the two valuable substances di- and mono-Arg, which are moreover degraded again in a secondary reaction, is clearly lower.

Example 4

A volume of 1 l of the preproinsulin solution having a concentration of 0.83 mg/ml is introduced into a glass beaker. After a pH of 8.3 has been set, the cleavage reaction is started by addition of the trypsin attached to a Eupergit® C1Z in a concentration of 0.081 U/ml. The temperature of the solution is 6° C. over the entire reaction period. The pH is kept constant during the reaction by addition of 1 M NaOH solution. Samples of the reaction solution are withdrawn at regular intervals over a period of 23 h and the content of the individual reaction components is determined by means of HPLC.

Figure 4:
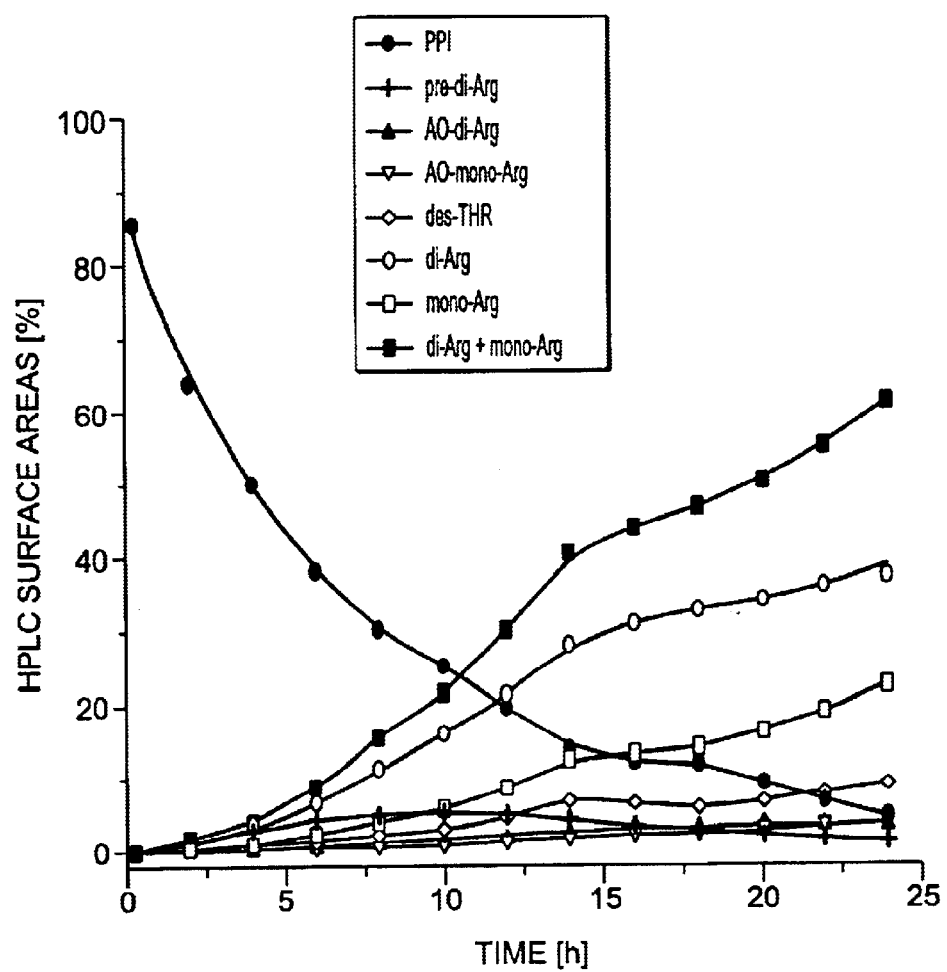

As can be seen in FIG. 4, the two desired valuable substances di- and mono-Arg are formed in an excess in contrast to the prior reaction experiments with immobilized trypsin based on this support, while the proportion of the by-products (in particular des-Thr) is drastically reduced.

Example 5

A volume of 1 l of the preproinsulin solution having a concentration of 0.83 mg/mil is introduced into a glass beaker. After a pH of 8.3 has been set, the cleavage reaction is started by addition of the trypsin attached to Eupergit® C1Z in a concentration of 0.405 U/ml. The temperature of the solution is 6° C. over the entire reaction period. The pH is kept constant during the reaction by addition of 1 M NaOH solution. Samples of the reaction solution are withdrawn at regular intervals over a period of 12 h and the content of the individual reaction components is determined by means of HPLC. The desired product and by-product spectrum also results in this example on use of the trypsin immobilized on Eupergit® C1Z.

Figure 5:
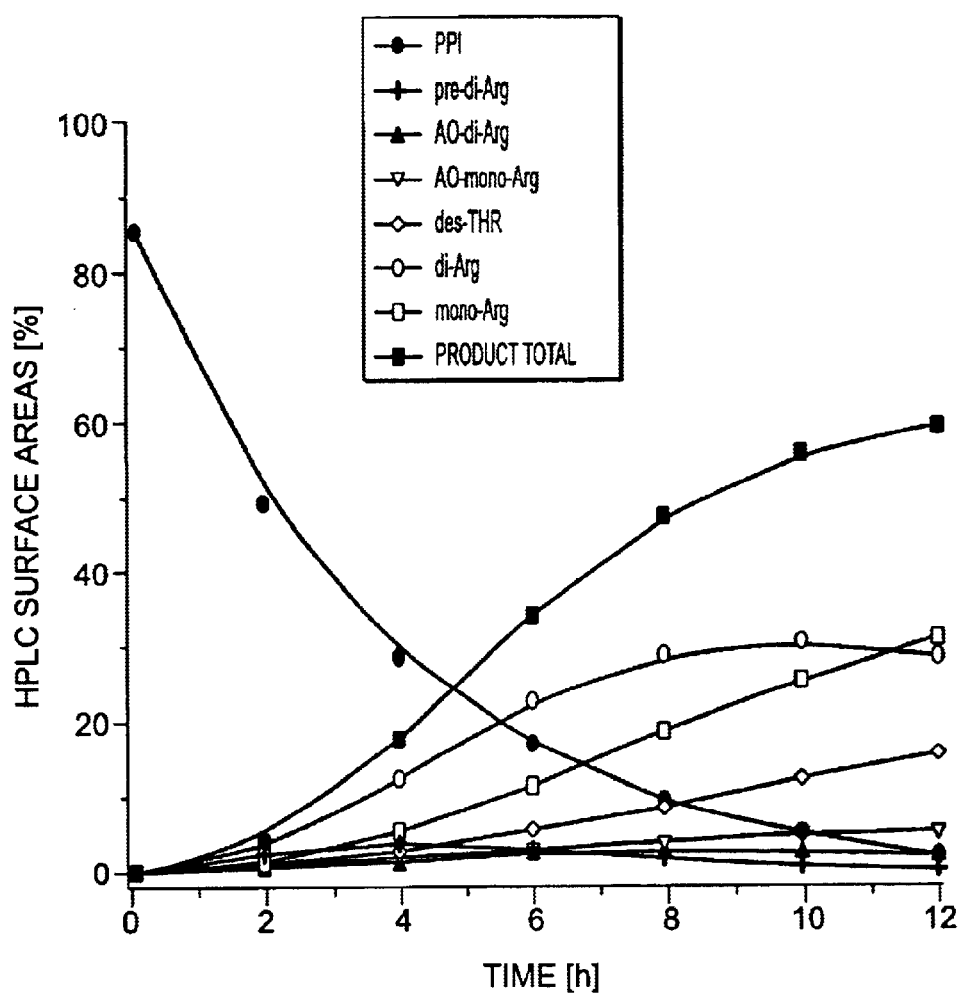

As can be seen in FIG. 5, by quintupling the catalyst concentration the reaction rate can be increased and thus the reaction time needed can be markedly shortened without the selectivity of the reaction thereby being shifted to the disfavor of the two valuable substances.

Possible interpretation of the results of Examples 2 to 5

Figure 6:
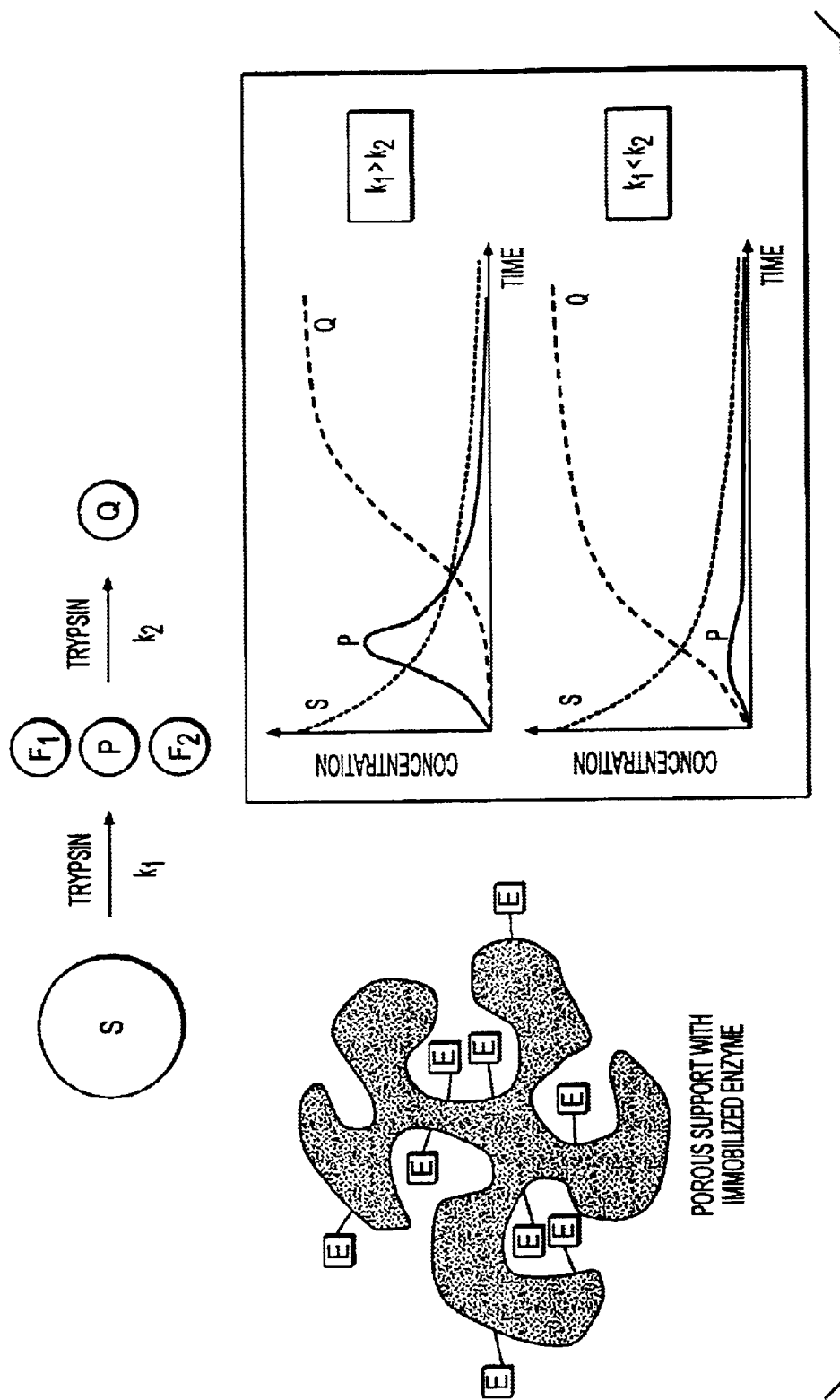

For example, in the case of preproinsulins (PPI) the starting substrate, in contrast to the secondary products of the reaction, is a larger molecule ($\cong$10 kDa), which is subject to a greater pore diffusion limitation. For this reason, the reaction rate of all secondary reactions is greater than the direct reaction of PPI in different fragments. In the case of supports encumbered with pores, for this reason an accumulation of the desired intermediate P (see FIG. 6; in this ex.: di-Arg) should not be possible. The use of pore-free (or almost pore-free) supports therefore offers itself as an approach to the solution of the control of the selectivity.

Figure 1B:
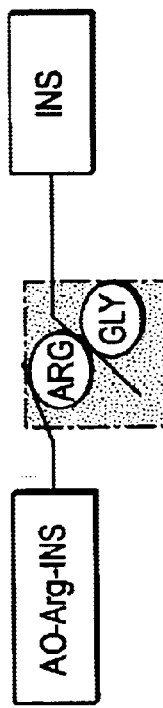
Figure 1D:
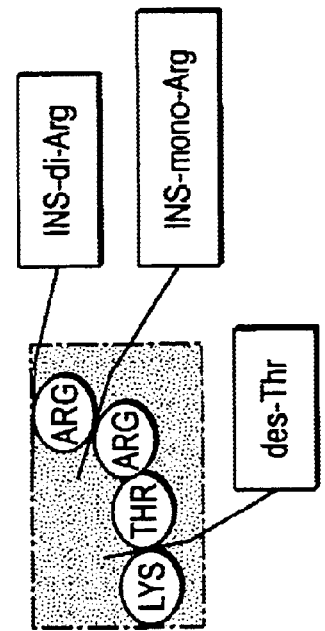
Figure 1C:
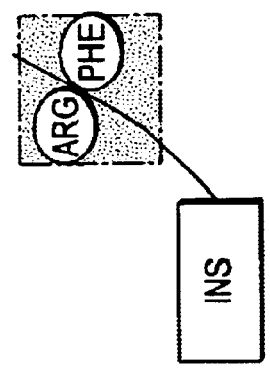

Legend to Figures:

FIG. 1A–FIG. 1D: Reactive sites in the tryptic cleavage of preproinsulin (INS=insulin (FIG. 1B and FIG. 1C); AO-Arg-INS=Arg(AO)-insulin (FIG. 1B); INS-di-Arg=Arg(B31), Arg(B32)-insulin (FIG. 1D); INS-mono-Arg=Arg(B31)-insulin (FIG. 1D); des-Thr=des(B30)-insulin (FIG. 1D).

FIG. 2: Course of the concentrations of the reaction components as a function of time in the cleavage of pre-proinsulin using trypsin immobilized on Deloxan®

FIG. 3: Course of the concentrations of the reaction components as a function of time in the cleavage of pre-proinsulin using trypsin immobilized on Eupergit® C250L FIG. 4: Course of the concentrations of the reaction components as a function of time in the cleavage of pre-proinsulin using trypsin immobilized on Eupergit® C1Z FIG. 5: Course of the concentrations of the reaction components as a function of time in the cleavage of pre-proinsulin using trypsin immobilized on Eupergit® C1Z FIG. 6: Significance of the support morphology for the selectivity of the reaction (S=substrate, e.g. PPl; P=desired intermediate, e.g. di-Arg; Q=undesired secondary product, e.g. des-Thr)

What is claimed is:

1. A process for enzymatic extraction of an insulin or an analog thereof comprising:
   preparing a preproinsulin solution;
   adding to said solution a non-porous polymeric support having at least one enzyme bonded thereto wherein the enzyme cause a reaction in which an insulin or an analog thereof is cleaved from the preproinsulin solution;
   recovering said insulin or analog thereof from the solution; and
   wherein said insulin analog retains insulin activity.

2. The process as claimed in claim 1, wherein the enzyme is bonded covalently to the support material with the aid of oxirane groups.

3. The process as claimed in claim 1, wherein the enzyme is trypsin.

4. The process as claimed in claim 3, wherein said enzyme has an activity of 0.05 to 0.5 U/ml.

5. The process as claimed in claim 1, wherein the enzyme immobilized on the support has an activity of 0.05 to 0.5 U/ml.

6. The process as claimed in claim 1, wherein the pH of the reaction is 6 to about 10.

7. The process as claimed in claim 6, wherein the pH is in the range of about 7 to about 9.

8. The process as in claim 1, wherein the non-porous polymeric support material is a copolymer of the monomers methacrylamide and N,N'-bis(methacrylamide).

9. The process as in claim 8, wherein the non-porous polymeric support material has oxirane group-containing monomers.

* * * * *